(12) United States Patent
Arab et al.

(10) Patent No.: US 10,486,155 B1
(45) Date of Patent: Nov. 26, 2019

(54) VACUUM-LOADED, DROPLET-GENERATING MICROFLUIDIC CHIPS AND RELATED METHODS

(71) Applicant: KLARIS CORPORATION, Austin, TX (US)

(72) Inventors: Nicolas Arab, Austin, TX (US); Ross Johnson, Austin, TX (US); David Bussian, Austin, TX (US); Jon Isom, Austin, TX (US)

(73) Assignee: KLARIS CORPORATION, Austin, TX (US)

( * ) Notice: Subject to any disclaimer, the term of this patent is extended or adjusted under 35 U.S.C. 154(b) by 0 days.

(21) Appl. No.: 16/252,304

(22) Filed: Jan. 18, 2019

Related U.S. Application Data

(60) Provisional application No. 62/748,919, filed on Oct. 22, 2018.

(51) Int. Cl.
*B01L 3/00* (2006.01)

(52) U.S. Cl.
CPC ..... *B01L 3/50273* (2013.01); *B01L 3/502715* (2013.01); *B01L 3/502784* (2013.01); *B01L 2200/027* (2013.01); *B01L 2200/0605* (2013.01); *B01L 2200/0642* (2013.01); *B01L 2200/0673* (2013.01); *B01L 2200/0684* (2013.01); *B01L 2200/0689* (2013.01); *B01L 2400/0403* (2013.01); *B01L 2400/049* (2013.01)

(58) Field of Classification Search
CPC ......... B01L 2300/0864; B01L 3/50273; B01L 3/502784; B01L 3/502715; B01L 2200/0642; B01L 2200/0673; B01L 2200/0605; B01L 2200/027; B01L 2200/0684; B01L 2400/049; B01L 2400/0403
See application file for complete search history.

(56) References Cited

U.S. PATENT DOCUMENTS

| 5,609,828 | A | 3/1997 | O'Bear et al. |
| 5,762,873 | A | 6/1998 | Fanning et al. |
| 5,965,090 | A | 10/1999 | Fanning et al. |
| 7,150,999 | B1 * | 12/2006 | Shuck ............ G01N 35/10 436/180 |

(Continued)

FOREIGN PATENT DOCUMENTS

WO  WO 2016/170126  10/1916

*Primary Examiner* — Christopher Adam Hixson
(74) *Attorney, Agent, or Firm* — Norton Rose Fulbright US LLP

(57) ABSTRACT

A microfluidic chip that can have a body defining a microfluidic network including a test volume, one or more ports, and one or more channels in fluid communication between the port(s) and the test volume is described. Gas can be removed from the test volume before a sample liquid is introduced therein by reducing pressure at a first one of the port(s), optionally while the liquid is disposed in the port. Liquid in the first port can be introduced into the test volume by increasing pressure at the first port. The microfluidic network can define one or more droplet-generating regions in which at least one of the channel(s) defines a constriction and/or two or more of the channels connect at a junction. Liquid flowing from the first port can pass through at least one of the droplet-generating region(s) and to the test volume.

18 Claims, 14 Drawing Sheets

(56) References Cited

U.S. PATENT DOCUMENTS

| | | |
|---|---|---|
| 9,089,844 B2 | 7/2015 | Hiddessen et al. |
| 9,126,160 B2 | 9/2015 | Ness et al. |
| 9,216,392 B2 | 12/2015 | Hindson et al. |
| 9,347,059 B2 | 5/2016 | Saxonov |
| 9,500,664 B2 | 11/2016 | Ness et al. |
| 9,636,682 B2 | 5/2017 | Hiddessen et al. |
| 9,649,635 B2 | 5/2017 | Hiddessen et al. |
| 2016/0001289 A1* | 1/2016 | Hung ............... B01L 3/502784 436/180 |
| 2016/0257990 A1* | 9/2016 | Di Carlo ............. C12Q 1/6804 |

* cited by examiner

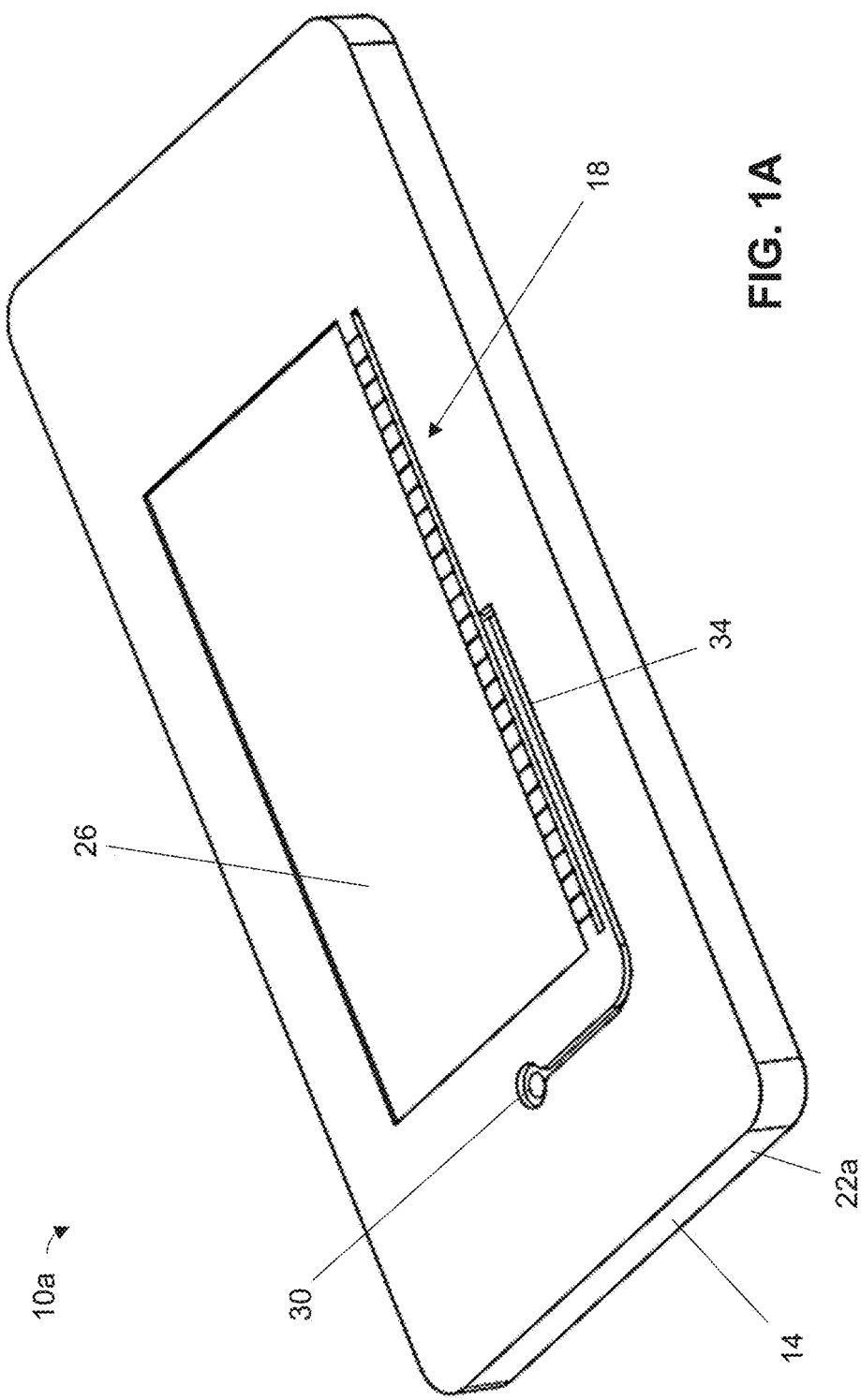

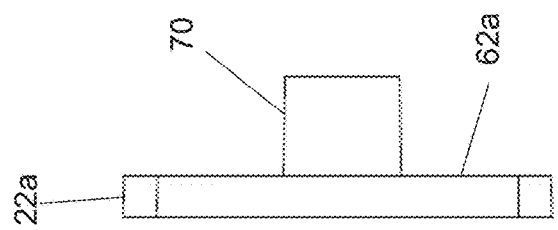
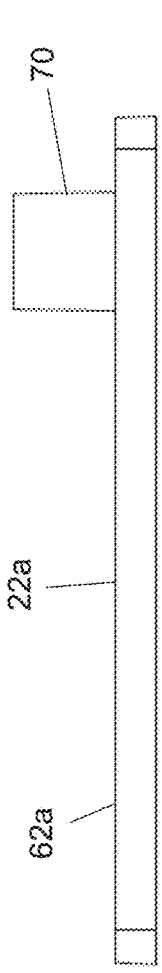
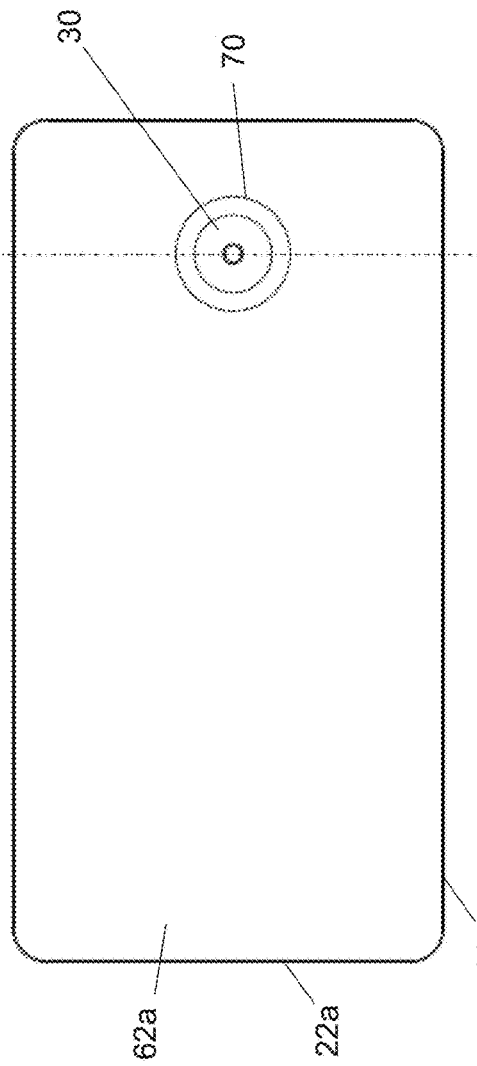
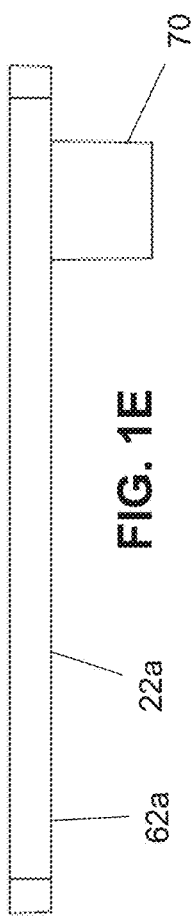
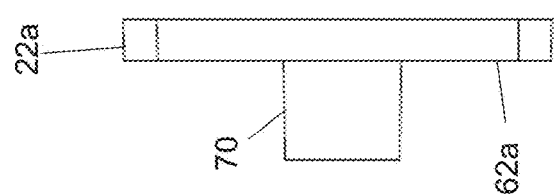

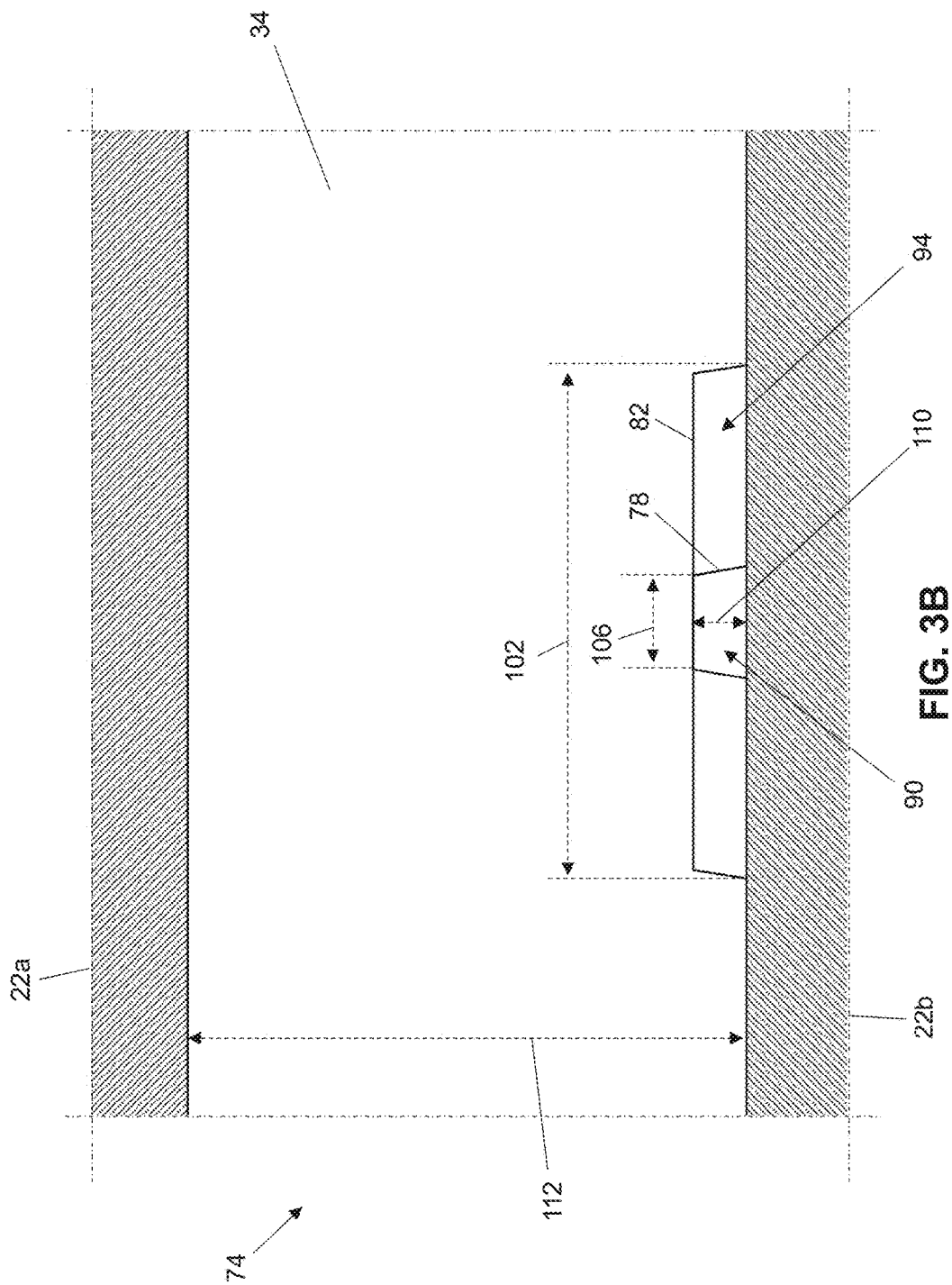

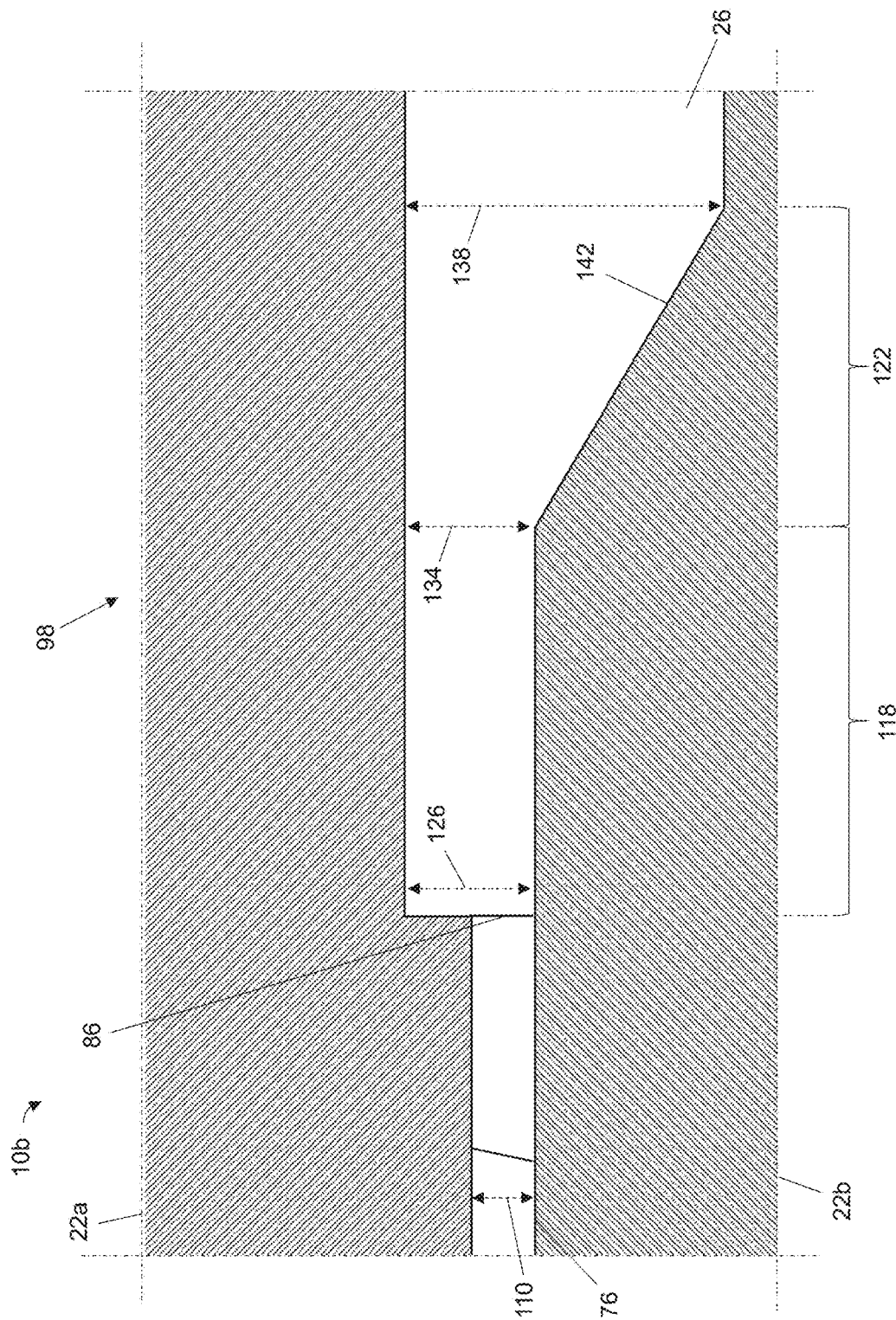

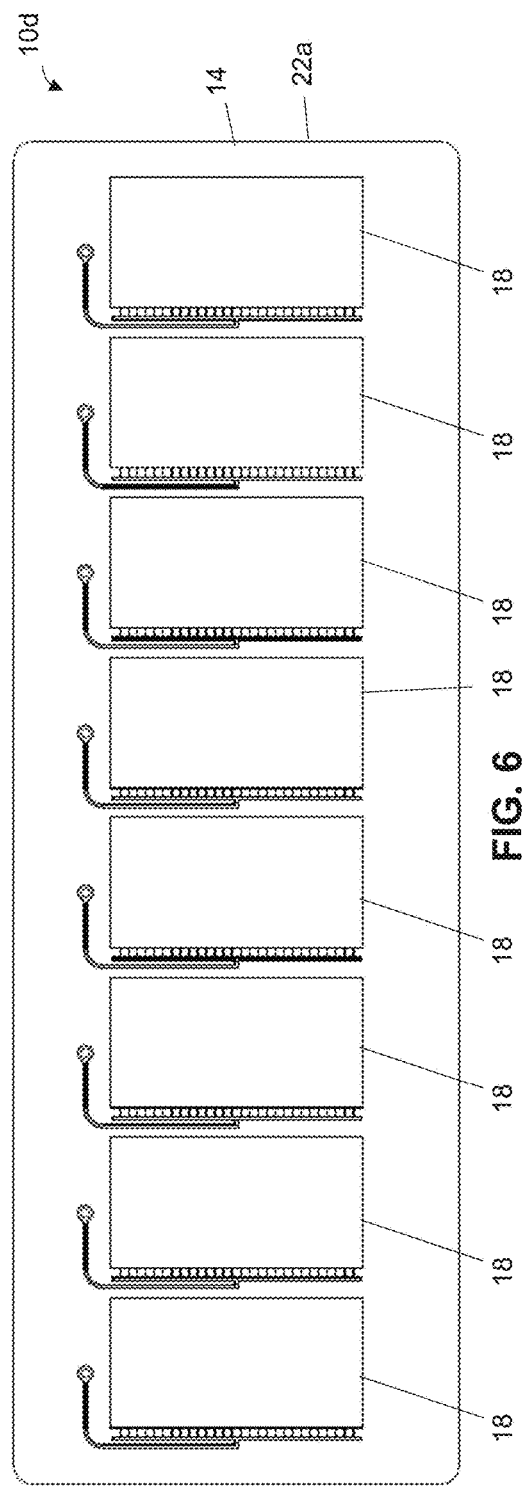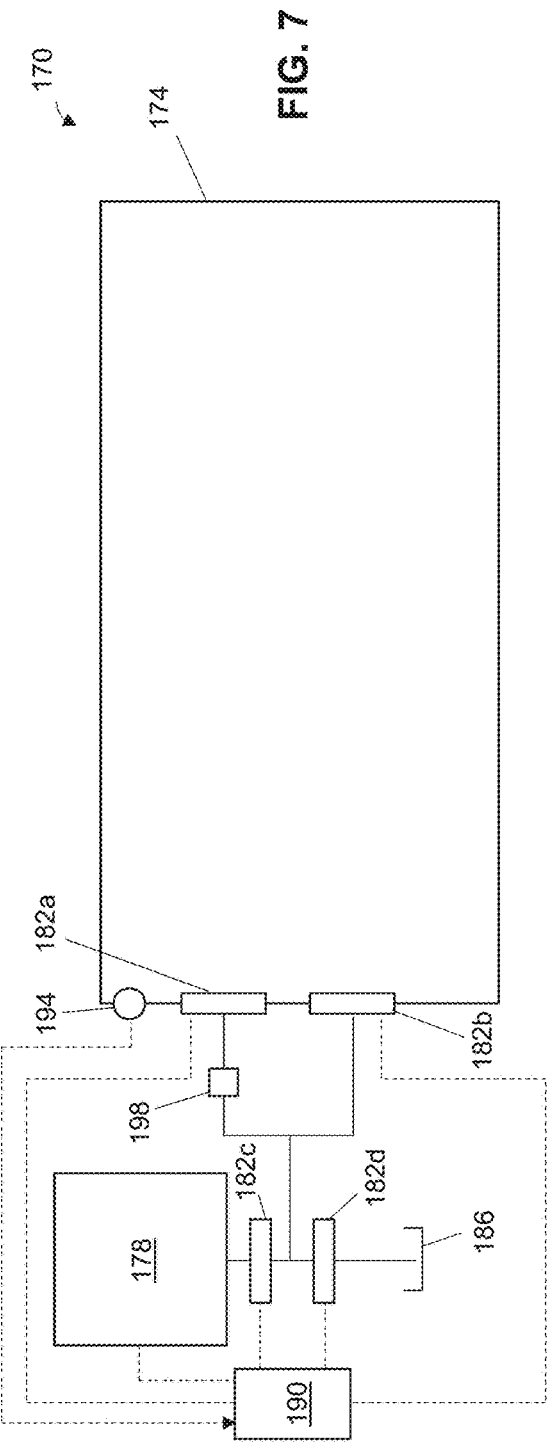

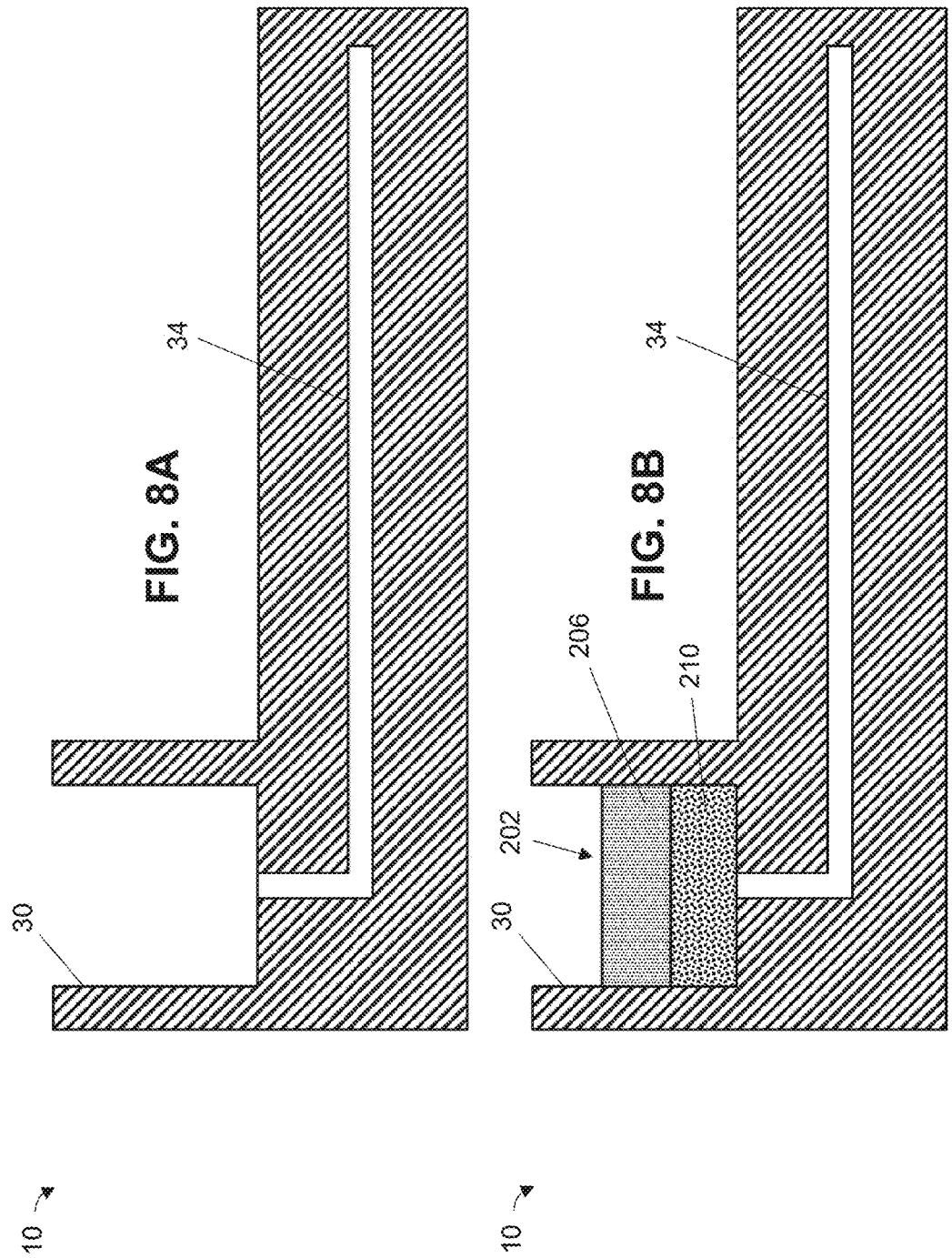

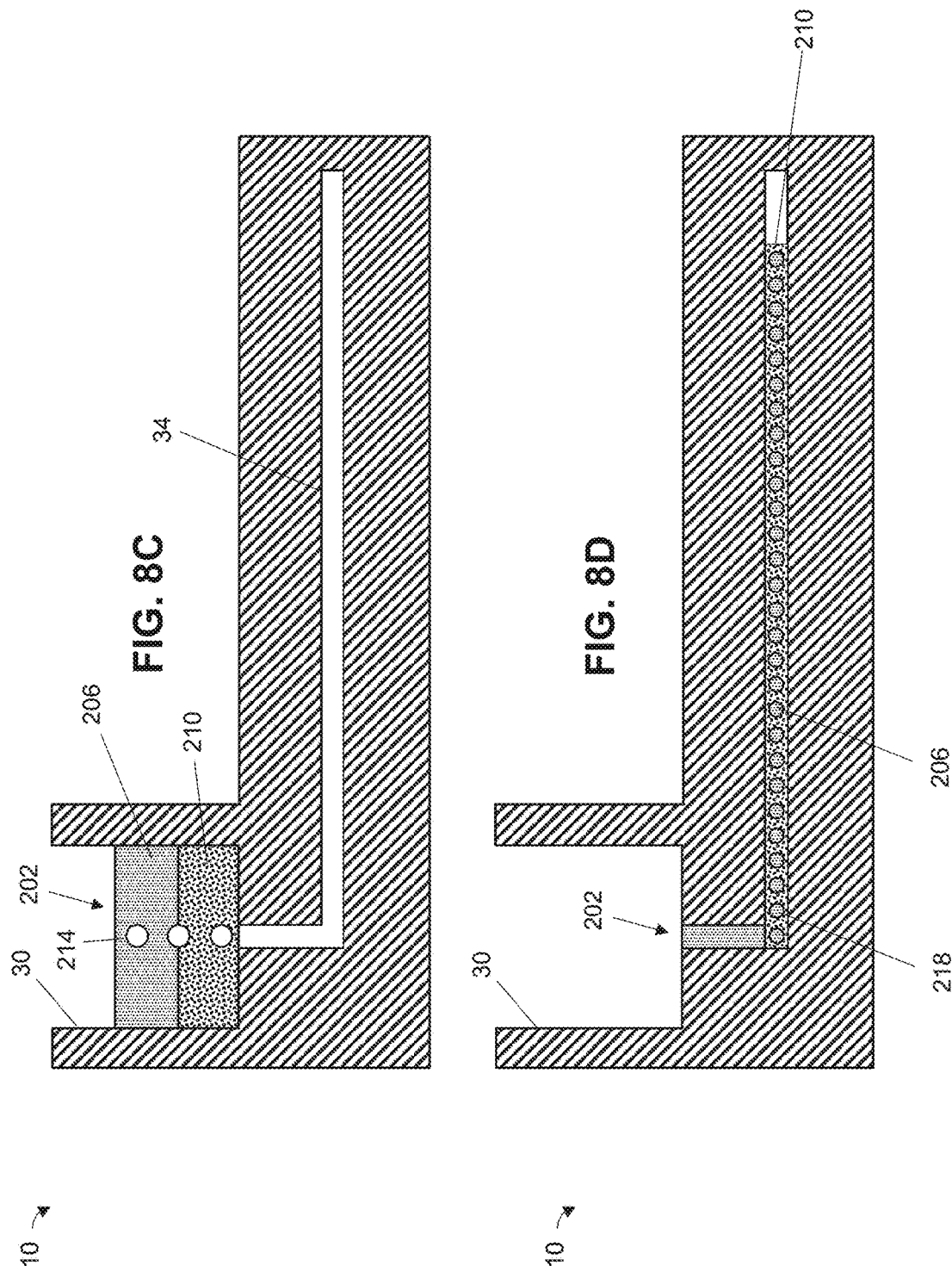

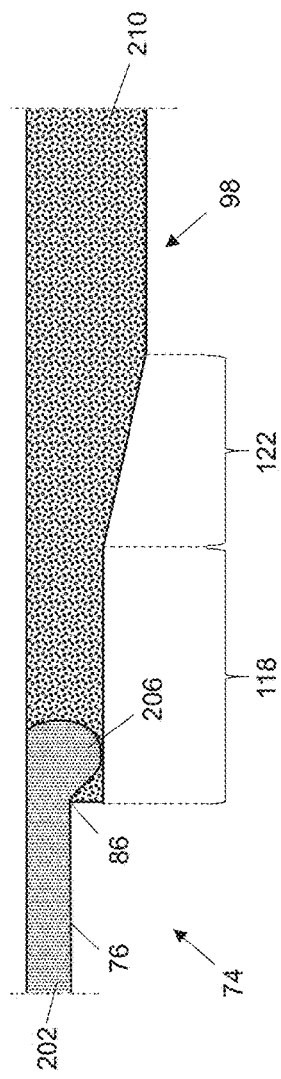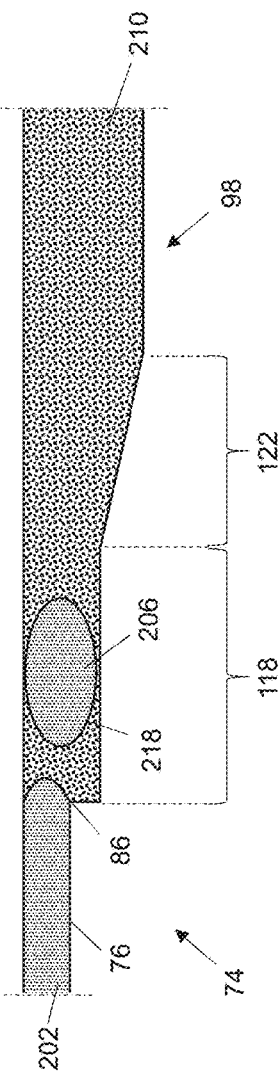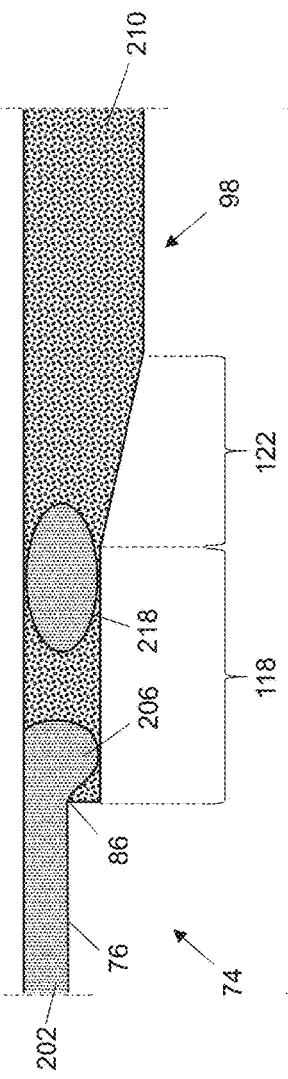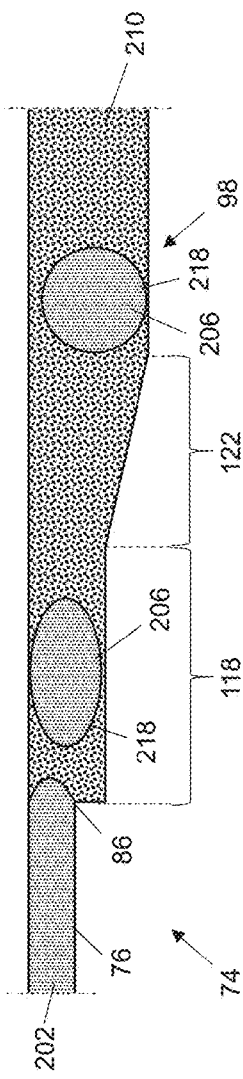

VACUUM-LOADED, DROPLET-GENERATING MICROFLUIDIC CHIPS AND RELATED METHODS

FIELD OF INVENTION

The present invention relates generally to microfluidic chips and, more particularly but without limitation, to droplet-generating microfluidic chips configured to be loaded using a vacuum and methods of loading the same.

BACKGROUND

Microfluidic chips have gained increased use in a wide variety of fields, including cosmetics, pharmaceuticals, pathology, chemistry, biology, and energy. A microfluidic chip typically has one or more channels that are arranged to transport, mix, and/or separate one or more samples for analysis thereof. At least one of the channel(s) can have a dimension that is on the order of a micrometer or tens of micrometers, permitting analysis of comparatively small (e.g., nanoliter or picoliter) sample volumes. The small sample volumes used in microfluidic chips provide a number of advantages over traditional bench top techniques. For example, more precise biological measurements, including the manipulation and analysis of single cells and/or molecules, may be achievable with a microfluidic chip due to the scale of the chip's components. Microfluidic chips can also provide improved control of the cellular environment therein to facilitate experiments related to cellular growth, aging, antibiotic resistance, and the like. And, microfluidic chips, due to their small sample volumes, low cost, and disposability, are well-suited for diagnostic applications, including identifying pathogens and point-of-care diagnostics.

In some applications, microfluidic chips are configured to generate droplets to facilitate analysis of a sample. Droplets can encapsulate cells or molecules under investigation to, in effect, amplify the concentration thereof and to increase the number of reactions. Droplet-based microfluidic chips may accordingly be well-suited for high throughput applications, such as chemical screening and PCR. The manner in which droplets are formed and arranged, however, may affect the analysis of the encapsulated cells or molecules. In at least some applications, the formed droplets should be substantially the same size and/or should not be stacked on one another such that the droplets form a two-dimensional array. Conventional droplet-generating microfluidic chips may be unable to provide this droplet size consistency or arrangement, particularly when the chips are mass-produced. For example, some microfluidic chips form droplets by expanding a sample fluid along a ramp region having a progressively increasing cross-sectional area. Because the ramp geometry determines droplet size, the ramp angle must be defined with a high degree of precision to form consistently-sized droplets. Many manufacturing methods, such as lithographic-based methods, can be used to precisely define some chip features (e.g., with sub-micron tolerances), but cannot provide such precision when forming angled features (e.g., ramps). As such, the manufacturing techniques available to produce ramp-only designs are limited and may define some chip features (other than the ramp) with less precision.

The test volume of a microfluidic chip is traditionally loaded with a sample by increasing pressure at the chip's inlet port to above ambient pressure such that the sample flows to the test volume. Loading a chip in this manner creates a positive pressure in which the pressure in the test volume is higher than that of the ambient environment. This can pose challenges. For example, the positive pressure may tend to separate seals of the microfluidic chip and may exacerbate leaks by permitting high-pressure gas to escape to the ambient environment, which can pose a safety risk when a sample includes pathogenic biological samples. Due to the pressure differential between the ambient environment and the test volume, conventional microfluidic chips may require additional seals to maintain the position of liquids therein.

These microfluidic chips generally have a second port downstream of the test volume to equalize pressure between the test volume and the ambient environment after droplet formation. During pressure equalization, at least a portion of the fluid flowing from the inlet port flows through the test volume before exiting through the second port. To prevent droplet loss during pressure equalization, these chips may require additional mechanisms to retain droplets in the test volume. And, these chips may require the use of additional oil to prevent the droplets from being exposed to air during pressure equalization, which can increase costs.

Accordingly, there is a need in the art for microfluidic chips that can form consistently-sized droplets and that can be loaded without creating a positive pressure between the test volume and the ambient environment.

SUMMARY

The present microfluidic chips address the need in the art for improved sample loading by defining one or more microfluidic networks in which gas can be removed from a test volume before the sample is introduced therein. For some chips, at least one of the microfluidic network(s) can include a single port for both loading a sample liquid and removing gas from the test volume. Gas evacuation can occur while the liquid is disposed in the port by decreasing the pressure at the port (e.g., to below ambient pressure). After gas evacuation, the liquid can be introduced into the test volume by increasing the pressure at the port (e.g., to ambient pressure). The changes in pressure can be achieved using a vacuum chamber.

By removing gas before introducing the liquid into the test volume, the pressure in the test volume during loading can be less than that of the ambient environment such that a negative, rather than a positive, pressure exists between the test volume and the ambient environment. The negative pressure can reinforce seals of the chip and contain leaks. When loading is complete, the pressure in the test volume can equal the ambient pressure, obviating the need for seals to maintain the position of liquid in the test volume and for mechanisms to equalize the test volume pressure. As such, the present microfluidic chips can be loaded without using the additional oil that traditional chips use during pressure equalization, thereby reducing costs. The evacuated gas can pass through and agitate the liquid in the port to facilitate mixing of the sample.

The present microfluidic chips can also define one or more droplet-generating regions configured to form consistently-sized droplets. At least one of the droplet-generating region(s) can include a constriction section and, optionally, an expansion region having a minimum cross-sectional area larger than that of the constriction section. The expansion region can include a constant portion having a substantially constant cross-sectional area and an expanding portion having a ramp such that a cross-sectional area of the expanding portion increases moving away from the constant portion. Liquid flowing toward the test volume can pass through the constriction section and into the constant portion to form droplets. The expanding portion can be configured to propel the droplets out of the expansion region such that the droplets do not obstruct liquid flow from the constriction section to minimize droplet variations caused by obstructions. And, because droplet formation occurs in the constant portion, the angle of the ramp need not be defined with the level of precision required for ramp-only designs to achieve droplet consistency. As such, more manufacturing techniques, such as lithographic-based techniques, are available to produce the present chips than for ramp-only designs. The present microfluidic chips can accordingly achieve equivalent droplet consistency to traditional chips with less constraint on manufacturing methods. The additional manufacturing methods available to produce the present chips may define at least some chip features with greater precision and accuracy than the manufacturing methods that must be used for ramp-only designs.

Additionally or alternatively, at least one of the droplet-generating region(s) can comprise two or more channels that connect at a junction at which liquid flowing to the test volume from two or more respective ports can meet to form droplets. Unlike conventional two-port designs which incorporate a port downstream of the test volume for pressure equalization, all of the ports can be upstream of the test volume such that, for each of the ports, fluid can flow from the port to each other of the ports without flowing through the test volume. This configuration can permit gas evacuation through the ports and allow the ports to facilitate the droplet-generating functionality.

Some of the present methods of loading a microfluidic chip comprise disposing a liquid, which optionally comprises an aqueous liquid and a non-aqueous liquid, within a first one of one or more ports of a microfluidic network of the chip. Some of the present microfluidic chips comprise a body and one or more microfluidic networks defined by the body. At least one of the network(s), in some embodiments, includes one or more ports, optionally a single port (e.g., the one or more ports consist of the first port), or further optionally two or more ports. At least one of the network(s), in some embodiments, includes a test volume. Optionally, when the port(s) comprise two or more ports, the network is configured such that, for each of the ports, fluid is permitted to flow from the port to each other of the ports without flowing through the test volume. In some embodiments, at least one of the network(s) includes one or more channels, optionally two or more channels, in fluid communication between the port(s) and the test volume. The body, in some embodiments, comprises a planar portion having top and bottom faces connected by an edge. In some embodiments, the planar portion defines the test volume and the channel(s). In some embodiments, one or more protrusions extend from the top face and, optionally, each of the protrusion(s) defines at least a portion of at least one of the port(s).

In some embodiments, at least one of the network(s) defines a droplet-generating region in which at least one of the channel(s) defines a constriction and/or two or more of the channels connect at a junction. For some embodiments in which two or more of the channels connect at a junction, for each of at least two of the connecting channels, fluid is permitted to flow from at least one of the ports, through the connecting channel, and to the junction without flowing through any other of the connecting channels or the test volume.

Some methods comprise introducing at least a portion of the liquid into the test volume. In some methods, the introducing is performed at least by reducing pressure at the first port such that gas flows from the test volume, through at least one of the channel(s), and out of the first port. In some methods, reducing pressure at the first port is performed at least by reducing pressure within a vacuum chamber within which the chip is disposed. During reducing pressure at the first port, in some methods gas that flows out of the first port passes through the liquid. In some methods, prior to reducing pressure at the first port, pressure at the first port is substantially ambient pressure.

In some methods, the introducing is performed at least by increasing pressure at the first port such that the portion of the liquid flows from the first port, through at least one of the droplet-generating region(s), and into the test volume. Increasing pressure at the first port, in some methods, is performed at least by venting the vacuum chamber. In some methods, after increasing pressure at the first port, pressure at the first port is substantially ambient pressure. After introducing at least a portion of the liquid into the test volume, in some methods pressure within the test volume is substantially ambient pressure.

At least one of the network(s), for some embodiments, includes an expansion region. In some of such embodiments, in at least one of the droplet-generating region(s), at least one of the channel(s) comprises a constriction section that defines the constriction and is connected to the expansion region such that liquid is permitted to flow from the port, pass through the constriction section, and exit the constriction section into the expansion region. In some embodiments, a minimum cross-sectional area of the expansion region is greater than or equal to 110% of a minimum cross-sectional area of the constriction section, taken perpendicularly to the centerline of the constriction section. For some embodiments, the expansion region has a minimum height that is greater than or equal to 150% of a maximum height of each of the constriction section(s), taken perpendicularly to the centerline of the constriction section. In some embodiments, the expansion region has a constant portion and an expanding portion such that liquid is permitted to exit at least one of the constriction section(s) into the constant portion and flow to the expanding portion. In some of such embodiments, the constant portion has a height that is substantially the same between the constriction section and the expanding portion and, optionally, is substantially equal to the minimum height of the expansion region. The expanding portion, in some embodiments, has a height that increases moving away from the constant portion.

In some methods, when pressure at the first port is increased, the portion of the liquid flows from the first port, passes through the constriction section, and exits the constriction section into the expansion region. In some methods where the expansion region has a constant portion and an expanding portion, when the portion of the liquid exits the constriction section, the portion of the liquid enters into the constant portion and flows to the expanding portion.

In some embodiments, for each of the port(s) (e.g., for the first port), the port has a minimum cross-sectional area, taken perpendicularly to the centerline of the port, and for each of the channel(s) connected to the port, the portion of the channel that connects to the port has a minimum cross-sectional area, taken perpendicularly to the centerline of the portion of the channel, that is less than or equal to 90% of the minimum cross-sectional area of the port. Each of the channel(s), in some embodiments, has a maximum transverse dimension, taken perpendicularly to the centerline of the channel, that is less than 2 millimeters (mm).

The term "coupled" is defined as connected, although not necessarily directly, and not necessarily mechanically; two items that are "coupled" may be unitary with each other. The terms "a" and "an" are defined as one or more unless this disclosure explicitly requires otherwise. The term "substantially" is defined as largely but not necessarily wholly what is specified—and includes what is specified; e.g., substantially 90 degrees includes 90 degrees and substantially parallel includes parallel—as understood by a person of ordinary skill in the art. In any disclosed embodiment, the term "substantially" may be substituted with "within [a percentage] of" what is specified, where the percentage includes 0.1, 1, 5, and 10 percent.

The terms "comprise" and any form thereof such as "comprises" and "comprising," "have" and any form thereof such as "has" and "having," and "include" and any form thereof such as "includes" and "including" are open-ended linking verbs. As a result, an apparatus that "comprises," "has," or "includes" one or more elements possesses those one or more elements, but is not limited to possessing only those elements. Likewise, a method that "comprises," "has," or "includes" one or more steps possesses those one or more steps, but is not limited to possessing only those one or more steps.

Any embodiment of any of the apparatuses, systems, and methods can consist of or consist essentially of—rather than comprise/include/have—any of the described steps, elements, and/or features. Thus, in any of the claims, the term "consisting of" or "consisting essentially of" can be substituted for any of the open-ended linking verbs recited above, in order to change the scope of a given claim from what it would otherwise be using the open-ended linking verb.

Further, a device or system that is configured in a certain way is configured in at least that way, but it can also be configured in other ways than those specifically described.

The feature or features of one embodiment may be applied to other embodiments, even though not described or illustrated, unless expressly prohibited by this disclosure or the nature of the embodiments.

Some details associated with the embodiments described above and others are described below.

BRIEF DESCRIPTION OF THE DRAWINGS

The following drawings illustrate by way of example and not limitation. For the sake of brevity and clarity, every feature of a given structure is not always labeled in every figure in which that structure appears. Identical reference numbers do not necessarily indicate an identical structure. Rather, the same reference number may be used to indicate a similar feature or a feature with similar functionality, as may non-identical reference numbers. Views in the figures are drawn to scale, unless otherwise noted, meaning the sizes of the depicted elements are accurate relative to each other for at least the embodiment in the view.

FIG. 1A is a perspective view of a first embodiment of the present microfluidic chips having a body that defines a single microfluidic network that includes a single port, a test volume, and one or more channels in fluid communication between the port and the test volume. A second piece of the body that encloses the microfluidic network is not shown in FIG. 1A.

FIGS. 1B-1G are bottom, top, left, right, front, and rear views, respectively, of the microfluidic chip of FIG. 1A. A second piece of the body that encloses the microfluidic network is not shown in FIGS. 1B-1G.

FIG. 2 illustrates the relative sizes of the port and a portion of one of the channel(s) that is connected to the port.

FIG. 3B is a partial sectional view of the microfluidic chip of FIG. 1A taken along line 3B-3B of FIG. 3A. FIG. 3B illustrates the relative sizes of the constriction and the portion of the channel(s) connected to the constriction section.

FIG. 3C illustrates the geometry of the expansion region, which includes a constant portion and an expanding portion having a ramp defined by a plurality of steps.

FIG. 4 is a partial sectional view of a second embodiment of the present microfluidic chips and illustrates the expansion region thereof. The expansion region of the second microfluidic chip, as shown, is substantially similar to that shown in FIG. 3C, the primary exception being that the ramp of the expanding portion is defined by a different piece of the body and comprises a single planar surface.

FIG. 6 is a bottom view of a fourth embodiment of the present microfluidic chips in which the body defines a plurality of microfluidic networks. A second piece of the body that encloses the microfluidic network is not shown in FIG. 6.

FIG. 7 is a schematic of a system comprising a vacuum chamber that can be used to change the pressure at the port(s) of some of the present microfluidic chips to evacuate gas from and load liquid into the test volume of the chip. The system can include a vacuum source, one or more control valves, and a controller to adjust the rate at which a vacuum is created or vented.

FIGS. 8A-8D are schematics illustrating some of the present methods of loading a microfluidic chip, where liquid is loaded into a port, gas is evacuated from the test volume through the liquid, and the liquid flows through at least one droplet-generating region to form droplets.

FIGS. 9A-9D are schematics illustrating droplet generation when liquid flows from a constriction section into an expansion region.

DETAILED DESCRIPTION OF ILLUSTRATIVE EMBODIMENTS

Figure 1B:
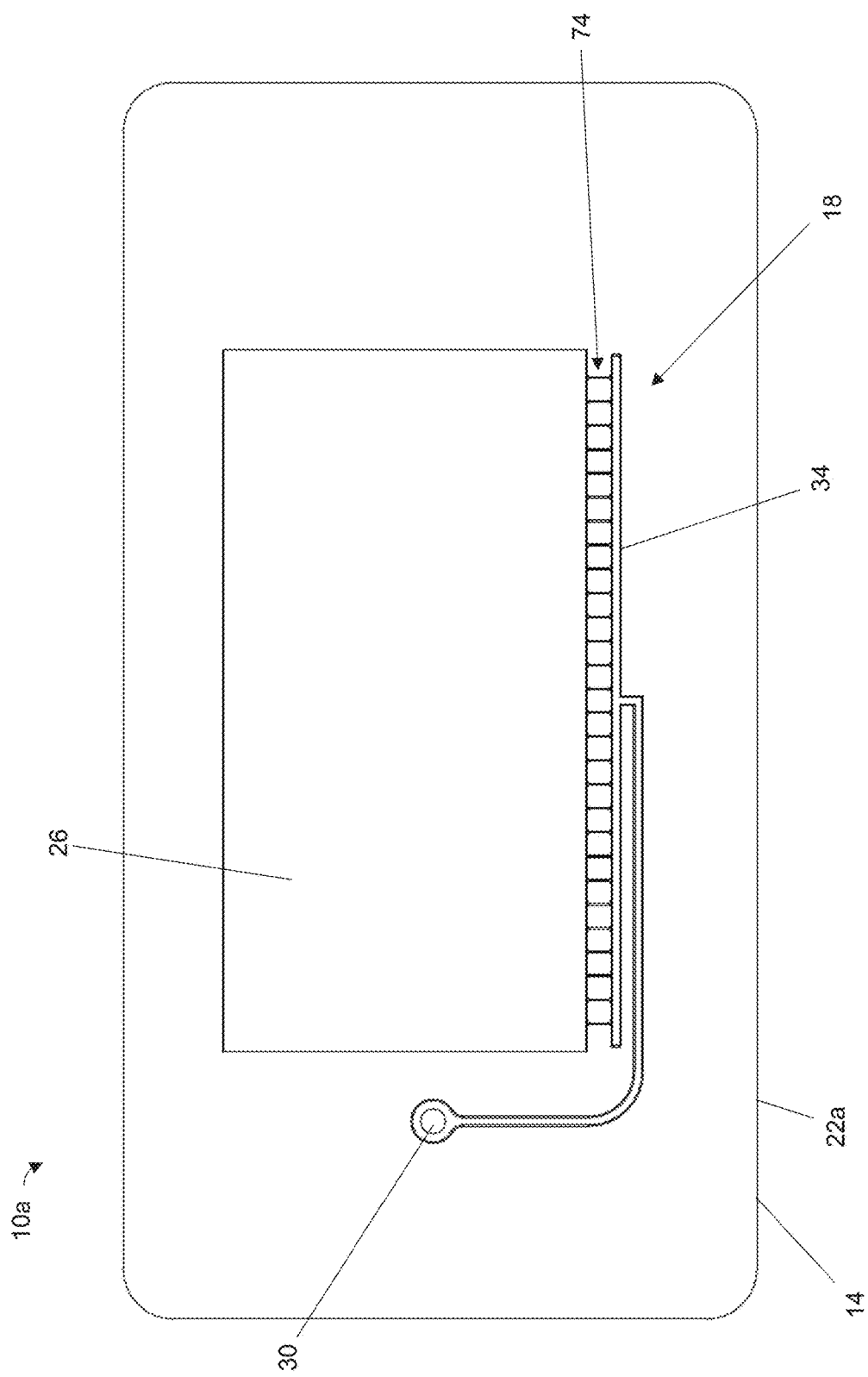

Referring to FIGS. 1A-1G, shown is a first embodiment 10a of the present microfluidic chips. Chip 10a can comprise a body 14 that defines a microfluidic network 18. Body 14 can comprise a single piece or can comprise multiples pieces (e.g., 22a and 22b), where at least one of the pieces defines at least a portion of microfluidic network 18. For example, body 14 of chip 10a comprises two pieces 22a and 22b (FIG. 2), only one of which is shown in FIGS. 1A-1G. Body 14 can comprise any suitable material; for example, at least one of pieces 22a and 22b can comprise a (e.g., rigid) polymer and, optionally, one of the pieces can comprise a polymeric film.

Microfluidic network 18 can include a test volume 26 configured to receive liquid for analysis. For example, chip 10a can be configured to permit identification of a pathogen encapsulated within microfluidic droplets disposed in test volume 26. In other embodiments, however, chip 10a can be used for any other suitable microfluidic application, such as, for example, DNA analysis, pharmaceutical screening, cellular experiments, electrophoresis, and/or the like.

Microfluidic network 18 can comprise a single port 30 and one or more channel(s) 34 in fluid communication between the port and test volume 26 such that liquids can be introduced into the test volume via the port. Port 30 and channel(s) 34 can be configured to permit evacuation of gas from test volume 26 before introducing liquid therein. For example, gas evacuation can be achieved while liquid is disposed in port 30 by reducing pressure at the port such that the gas in test volume 26 flows through at least one of channel(s) 34, through the liquid, and out of the port. The liquid can be introduced into test volume 26 (e.g., for analysis) by increasing pressure at port 30 such that the liquid flows from the port, through at least one of channel(s) 34, and into the test volume. In this manner, microfluidic network 18 can be configured to load liquid into test volume 26 using only a single port, thereby reducing manufacturing complexity. Each of channel(s) 34 can have any suitable maximum transverse dimension to facilitate microfluidic flow, such as, for example, a maximum transverse dimension, taken perpendicularly to the centerline of the channel, that is less than or equal to, or between any two of, 2 millimeters (mm), 1.5 mm, 1.0 mm, 0.5 mm, 300 micrometer ($\mu$m), 200 $\mu$m, 100 $\mu$m, 50 $\mu$m, 25 $\mu$m, or less.

Figure 2:
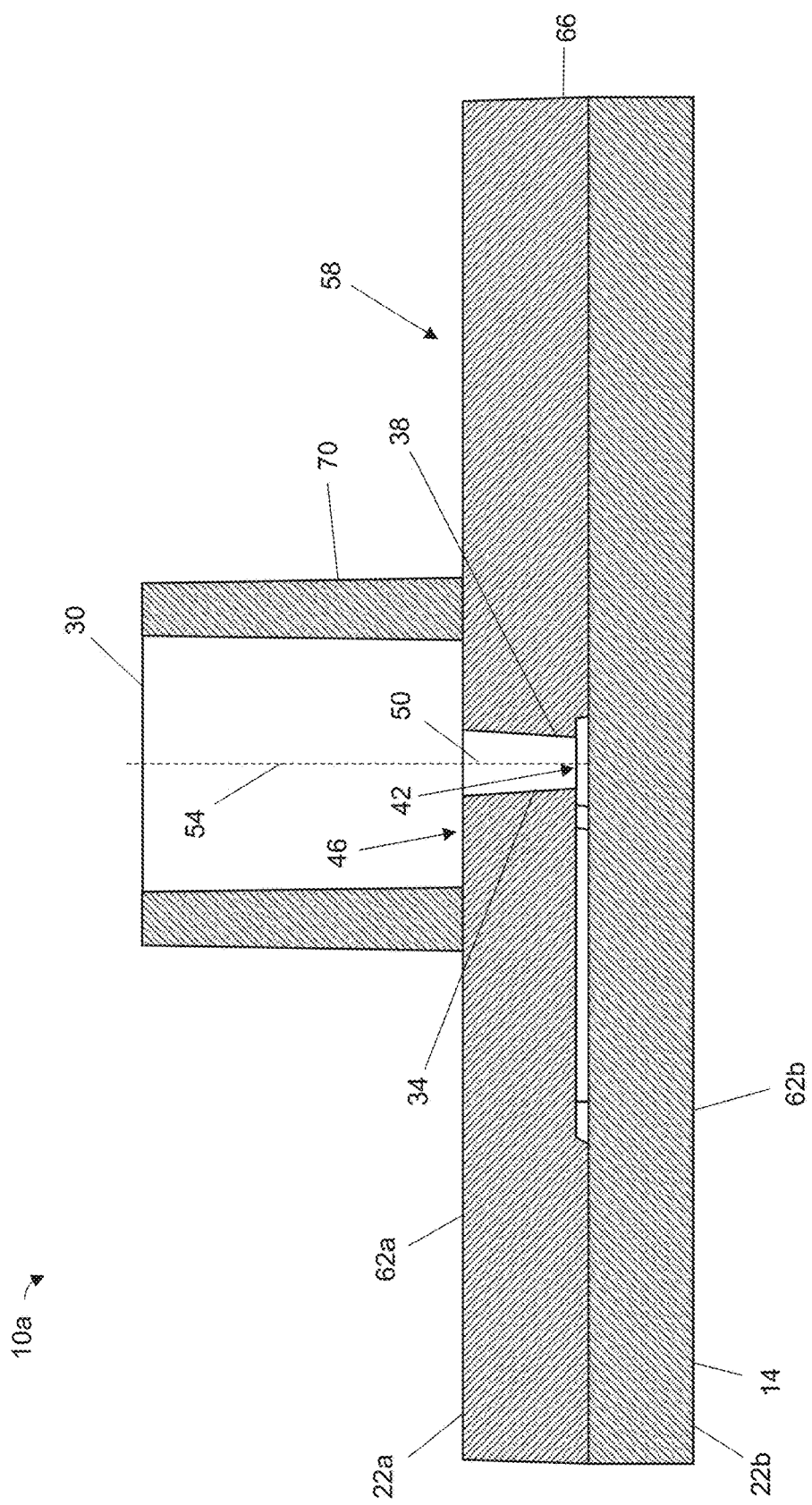
FIG. 2 is a sectional view of the microfluidic chip of FIG. 1A taken along line 2-2 of FIG. 1C.

Referring additionally to FIG. 2, port 30 and each of channel(s) 34 connected thereto can be shaped and sized to prevent loss of liquid from chip 10a during gas evacuation. To exit chip 10a via port 30, gas from test volume 26 may need to pass through liquid disposed in the port. Port 30 and channel(s) 34 are preferably configured such that the gas forms individual bubbles when progressing through the liquid to minimize or prevent liquid losses. If slug flow is produced instead, the gas may displace and remove the liquid from port 30. As such, each of channel(s) 34 connected to port 30 can have a portion 38 that connects the channel thereto and has a minimum cross-sectional area 42 (taken perpendicularly to centerline 50 of the portion) that is smaller than a minimum cross-sectional area 46 of the port (taken perpendicularly to centerline 54 of the port) to facilitate bubble flow and prevent or mitigate slug flow. For example, minimum cross-sectional area 42 of portion 38 can be less than or equal to, or between any two of, 90%, 80%, 66%, 60%, 46%, 40%, 30%, 20%, 10%, or less (e.g., less than or equal to 90% or 10%) of minimum cross-sectional area 46 of port 30. The smaller cross-sectional area of portion 38 can facilitate formation of gas bubbles having a diameter smaller than that of port 30 such that slug flow and thus liquid losses are mitigated during gas evacuation.

Liquid analysis may require a minimum volume of liquid disposed in test volume 26. Port 30 can be configured to receive and (e.g., at least temporarily) hold the requisite volume of liquid for introduction into test volume 26. For example, body 14 can comprise a planar portion 58 having top and bottom faces 62a and 62b connected by an edge 66, where a protrusion 70 extends from the top face and defines a portion of port 30. Protrusion 70 can thereby provide a raised area to facilitate introduction and temporary retention of liquid in chip 10a. Planar portion 58 can define test volume 26 and channel(s) 34 such that, during gas evacuation, the gas can rise through port 30 (e.g., through protrusion 70) and buoyancy can facilitate bubble formation.

Figure 3A:
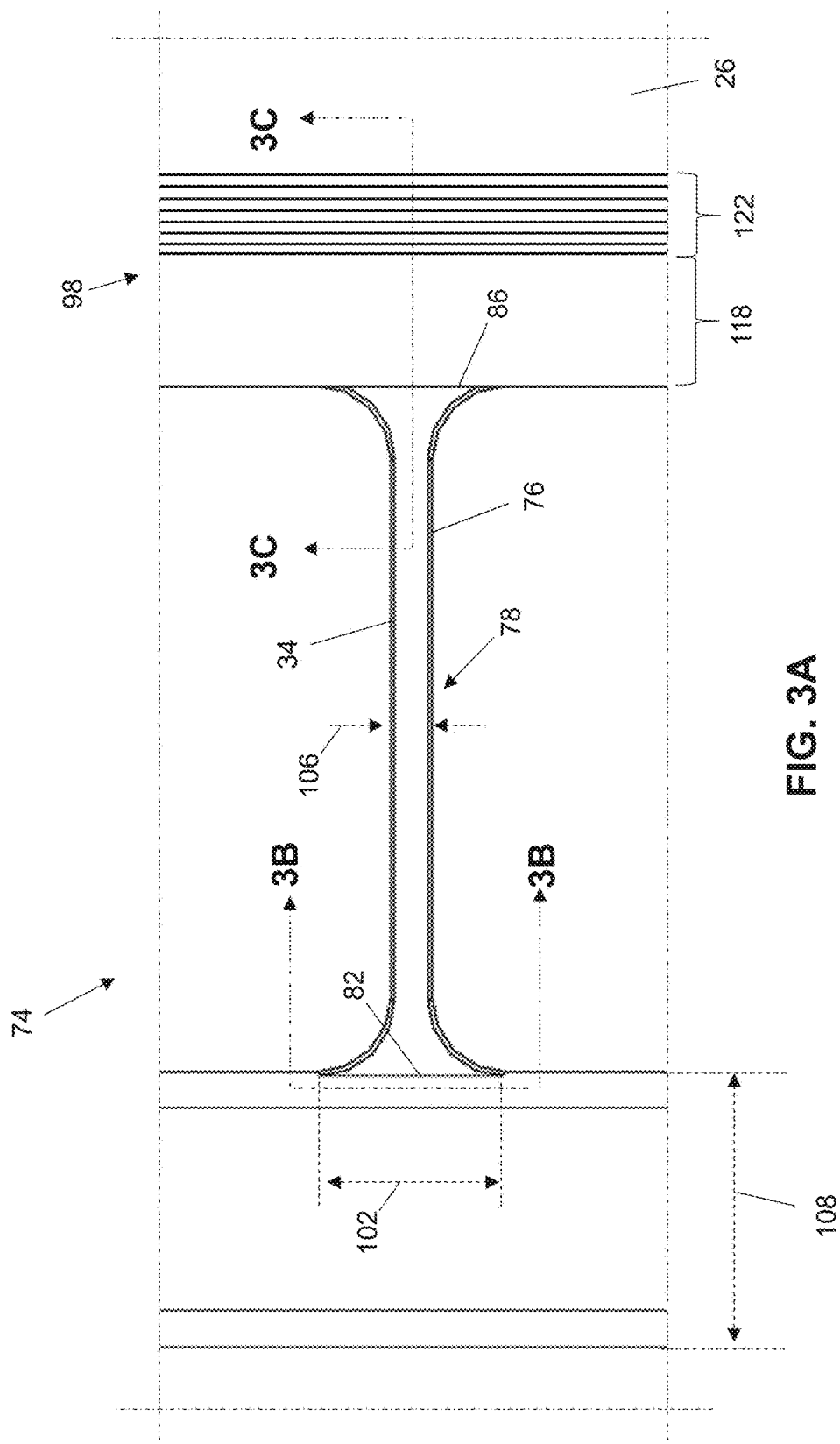
FIG. 3A is a partial, enlarged bottom view of one of the droplet-generating regions of the microfluidic chip of FIG. 1A in which at least one of the channel(s) has a constriction section that defines a constriction and is configured to communicate liquid to an expansion region to generate droplets.
Figure 3C:
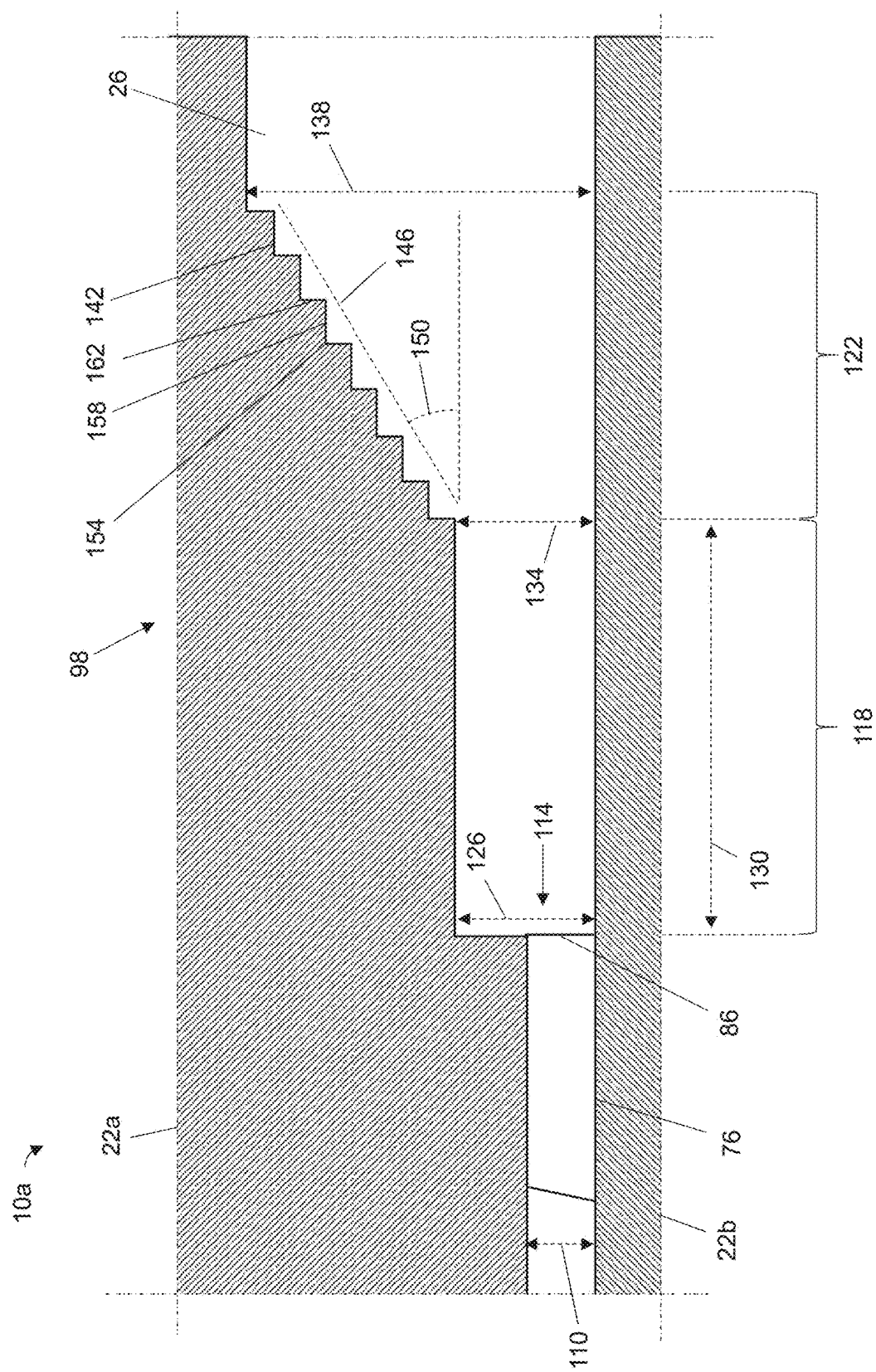
FIG. 3C is a partial sectional view of the microfluidic chip of FIG. 1A taken along line 3C-3C of FIG. 3A.

In some applications, analysis of liquid in test volume 26 may require the liquid to comprise droplets. Referring additionally to FIGS. 3A-3C, microfluidic network 18 can define one or more droplet-generating regions 74 that are configured to facilitate liquid droplet generation as liquid flows therethrough. As shown, for example, in at least one of droplet-generating region(s) 74, at least one of channel(s) 34 can have a constriction section 76 that defines a constriction 78. Each of constriction section(s) 76 can extend between a constriction inlet 82 and a constriction outlet 86, and can have a converging portion such that a minimum cross-sectional area 90 of the constriction section, taken perpendicularly to a centerline thereof, is smaller than a cross-sectional area 94 of the constriction section at constriction inlet 82. For example, minimum cross-sectional area 90 can be less than or equal to or between any two of 90%, 80%, 70%, 60%, 50%, 40%, 30%, 20%, 10%, or less (e.g., less than or equal to 25%) of cross-sectional area 94. Each of constriction section(s) 76 can have a maximum transverse dimension 102 (e.g., at constriction inlet 82 and, optionally, at constriction outlet 86), taken perpendicularly to the centerline of the constriction, that is less than or equal to, or between any two of, 200 $\mu$m, 175 $\mu$m, 150 $\mu$m, 125 $\mu$m, 100 $\mu$m, 75 $\mu$m, 50 $\mu$m, or less, and a minimum transverse dimension 106 (e.g., at constriction 78) that is less than or equal to, or between any two of, 40 $\mu$m, 35 $\mu$m, 30 $\mu$m, 25 $\mu$m, 20 $\mu$m, 15 $\mu$m, or less. Each of constriction section(s) 76 can have a maximum height 110, taken perpendicularly to the centerline and transverse dimension thereof, that is less than or equal to, or between any two of, 20 $\mu$m, 15 $\mu$m, 10 $\mu$m, 5 $\mu$m, or less.

A portion of at least one of channel(s) 34 that is connected to one of constriction inlet(s) 82 can have a maximum transverse dimension 108, taken perpendicularly to the centerline of the portion of the channel, and/or a maximum height 112, taken perpendicularly to the centerline and the transverse dimension thereof, that are larger than maximum transverse dimension 102 and maximum height 110, respectively, of constriction section 76. For example, at least one of maximum transverse dimension 108 and maximum height 112 can be greater than or equal to, or between any two of, 10 $\mu$m, 25 $\mu$m, 50 $\mu$m, 75 $\mu$m, 100 $\mu$m, 125 $\mu$m, 150 $\mu$m, 175 $\mu$m, 200 $\mu$m, or more (e.g., between 75 $\mu$m and 125 $\mu$m).

Droplet formation can be achieved by expanding the liquid following constriction thereof. Microfluidic network 18 can be configured such that, for each of constriction section(s) 76, liquid that flows from port 30 to test volume 26 can pass through the constriction section via constriction inlet 82 and exit the constriction section into an expansion region 98 via constriction outlet 86. Expansion region 98 can be defined by at least one of channel(s) 34 and/or by test volume 26; as shown, the test volume defines the expansion region. Expansion region 98 can have a minimum cross-sectional area 114 (e.g., taken at the interface between constriction outlet 86 and the expansion region) that is larger than minimum cross-sectional area 90 of constriction section 76. For example, minimum-cross sectional area 114 of expansion region 98 can be greater than or equal to or between any two of 110%, 150%, 200%, 300%, 400%, 500%, 1000%, 1500%, or more of minimum cross-sectional area 90. For example, a minimum height of expansion region 98 can be greater than or equal to, or between any two of, 150%, 200%, 250%, 300%, 350%, 400%, or more (e.g., greater than or equal to 300%) of maximum height 110 of constriction section 76, such as, for example, greater than or equal to or between any two of 5 µm, 20 µm, 35 µm, 50 µm, 65 µm, 80 µm or more. Liquid flowing from constriction section 76 into expansion region 98 can thereby expand and form droplets.

The geometry and size of expansion region 98 can be configured to promote formation of droplets of substantially the same size and to achieve a suitable droplet arrangement in test volume 26. As shown, expansion region 98 can have a constant portion 118 and an expanding portion 122 that are arranged such that liquid exiting constriction outlet 86 can enter and form droplets in the constant portion. The droplets can thereafter flow through expanding portion 122. Constant portion 118 can have a height 126 (e.g., taken at the interface between constriction outlet 86 and the constant portion) that is equal to the minimum height of expansion region 98 and a length 130 taken between the constriction outlet and expanding portion 122. The height (and, e.g., the cross-sectional area) of constant portion 118 can remain at least substantially constant along length 130. Length 130 can be any suitable length sufficient to permit droplet formation, such as, for example, a length that is greater than or equal to, or between any two of, 15 µm, 25 µm, 50 µm, 100 µm, 200 µm, 300 µm, 400 µm, 500 µm, or more. As sized, constant portion 118 can compress the droplets to prevent full expansion thereof. Constant portion 118 can thereby prevent the droplets from stacking on one another such that the droplets can be arranged in a two-dimensional array in test volume 26. Such an array can facilitate accurate analysis of the droplets.

Expanding portion 122 can expand such that, moving away from constant portion 118, the height (and, e.g., cross-sectional area) of the expanding portion increases from a first height 134 to a second height 138. First and second heights 134 and 138 can be, for example, the minimum and maximum heights of expansion region 98, respectively. To illustrate, expanding portion 122 can define a ramp 142 having a slope 146 that is angularly disposed relative to constant portion 118 by an angle 150 such that the expanding portion expands moving away from constant portion 118. Angle 150 can be greater than or equal to or between any two of 10°, 20°, 30°, 40°, 50°, 60°, 70°, 80°, or more (e.g., between 20° and 40°), as measured relative to a direction parallel to the centerline of constant portion 118. Ramp 142 can be defined by a plurality of steps 154 (e.g., as shown), each having an appropriate run 158 and rise 162 such that the ramp has a desired slope 146. Alternatively, ramp 142 can be defined by a (e.g., single) planar surface. Ramp 142 can extend from constant portion 118 to a point at which expansion region 98 reaches it maximum height. The maximum height of expansion region 98 (and, e.g., of test volume 26) (e.g., second height 138) can be greater than or equal to, or between any two of, 15 µm, 30 µm, 45 µm, 60 µm, 75 µm, 90 µm, 105 µm, 120 µm, or more (e.g., between 65 µm and 85 µm).

As sized and shaped, expanding portion 122 can mitigate blockage at constriction outlet 86. Compressed droplets flowing from constant portion 118 to expanding portion 122 can travel and decompress along ramp 142. The decompression can lower the surface energy of the droplet such that the droplet is propelled along ramp 142 and out of expanding portion 122. At least by propelling droplets out of expanding portion 122, ramp 142 can mitigate droplet accumulation at the interface between constriction outlet 86 and expansion region 98 such that the droplets do not obstruct subsequent droplet formation. Because such obstruction can cause inconsistencies in droplet size, expanding portion 122—by mitigating blockage—can facilitate formation of consistently-sized droplets, e.g., droplets that each have a diameter within 3-6% of the diameter of each other of the droplets.

The design of expansion region 98, e.g., by incorporating both a constant portion 118 and an expanding portion 122, can facilitate manufacturability of chip 10a to minimize variations between droplets generated by different mass-produced microfluidic networks. Droplet generation using an expansion region that only comprises a ramp, for example, may require precise definition of the ramp angle to achieve consistent droplet sizing. Only a limited number of manufacturing techniques can provide this level of precision for angled features like ramps. Because in chip 10a droplet generation and sizing occurs in constant portion 118 rather than in expanding portion 122, the chip can generate consistently-sized droplets even if ramp 142 and angle 150 are not defined with the level of precision required for ramp-only designs. Chip 10a can thereby be produced using manufacturing techniques that are unavailable for ramp-only designs, e.g., techniques that may define ramp 142 with comparatively less precision. Although such techniques may not be as precise with respect to angled features, they may nevertheless define other chip features (e.g., constant portion 118) with greater precision to achieve consistent droplet sizing between different mass-produced microfluidic networks 18, whether those microfluidic networks are part of the same chip or different chips.

To illustrate, chip 10a can be mass-produced using a cost-effective mold capable of providing a suitable level of manufacturing precision. Chip 10a can be compression injection molded using a mold produced lithographically, e.g., in which silicon is etched and used in an electroplating process to form the mold surface. Such a mold can provide manufacturing precision on the order of 1 µm, even if chip 10a comprises a comparatively large number of features (e.g., channel(s) 34, constriction section(s) 76, and/or the like). Other molds may be unable to provide such precision, such as molds produced using micro-milling in which a stock material is milled with a cutter to define the molding surface. For example, due to cutter wear, vibration, and heat, micro-milled molds may only be able to provide manufacturing precision on the order of 3 µm, or worse, when the chip to be formed has a relatively large number of features.

When a lithographically-produced mold is used to form chip 10a, ramp 142 can be defined by steps 154, rather than by a single planar surface. Due to the limitations of lithography, the manufacturing costs of doing so can be high and, at least for conventional chips having ramp-only expansion regions, may be cost-prohibitive. As such, the ramp-only design of conventional chips may limit the manufacturing options available for production thereof, e.g., to injection molding using less-precise, micro-milled molds. Because the design of chip 10a permits production using lithographically-produced molds, the chip can be manufactured with greater precision than conventional chips.

Port 30, channel(s) 34, test volume 26, and ramp 142 can each be defined by piece 22a of body 14. Referring additionally to FIG. 4, shown is a microfluidic chip 10b that is substantially similar to chip 10a, the primary exception being that piece 22b—rather than piece 22a—of body 14 defines ramp 142 and at least a portion of test volume 26. Piece 22b may be produced using a micro-milled mold such that the ramp comprises a single planar surface, and piece 22a can be formed from a lithographically-produced mold. Because precise alignment and sizing of ramp 142 may be non-critical for generating consistently-sized droplets, forming piece 22b with a micro-milled mold may have little, if any, impact of chip 10b's ability to produce consistently-sized droplets, and can reduce manufacturing costs. Forming piece 22a using a lithographically-produced mold can maintain a suitable level of manufacturing precision for chip 10b.

Figure 5A:
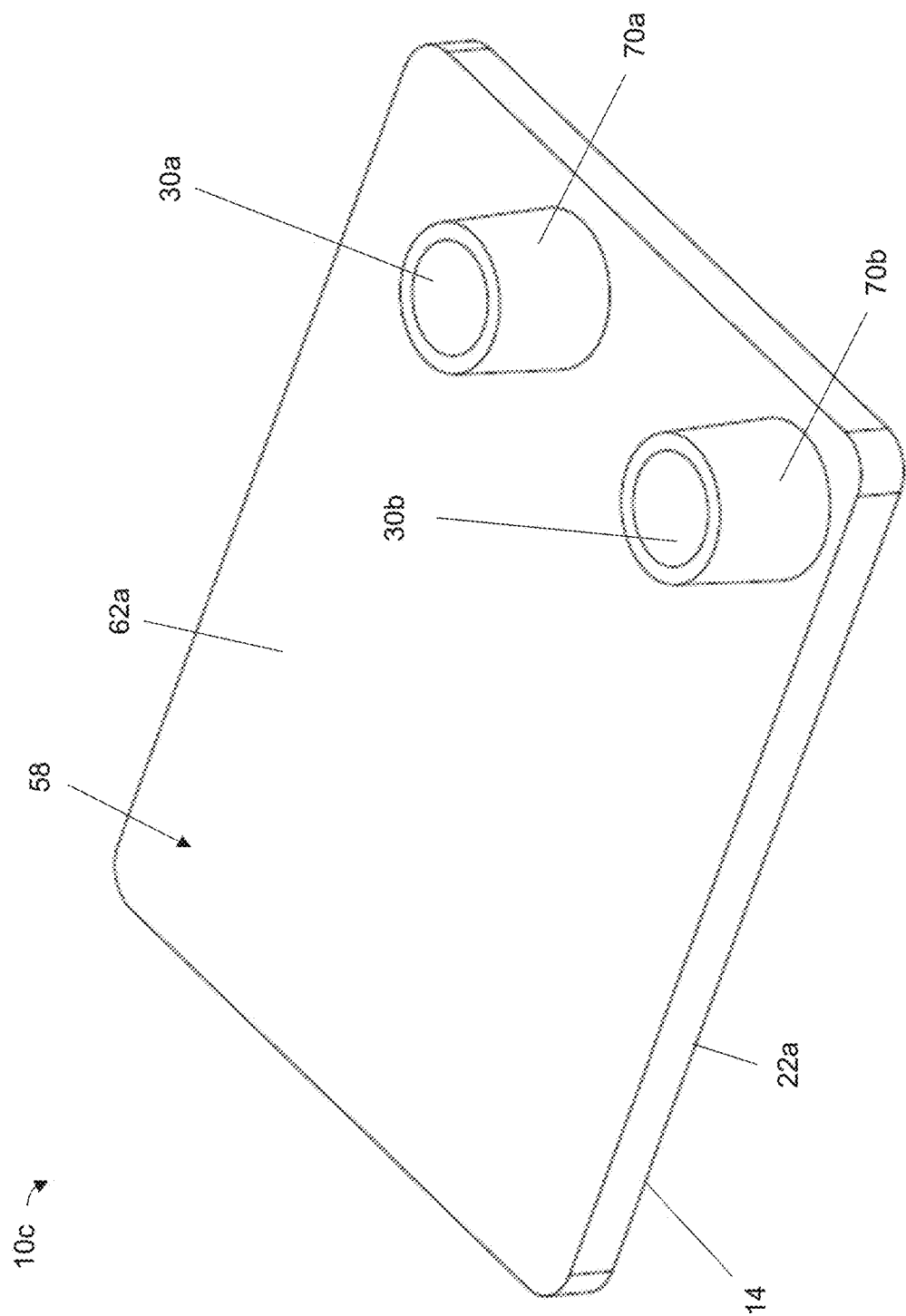
FIGS. 5A and 5B are perspective and bottom views, respectively, of a third embodiment of the present microfluidic chips in which at least one of the droplet-generating regions of the microfluidic network comprises a junction at which two or more channels are connected such that liquid flowing from two or more ports upstream of the test volume can meet at the junction to generate droplets. A second piece of the body that encloses the microfluidic network is not shown in FIGS. 5A and 5B.
Figure 5B:
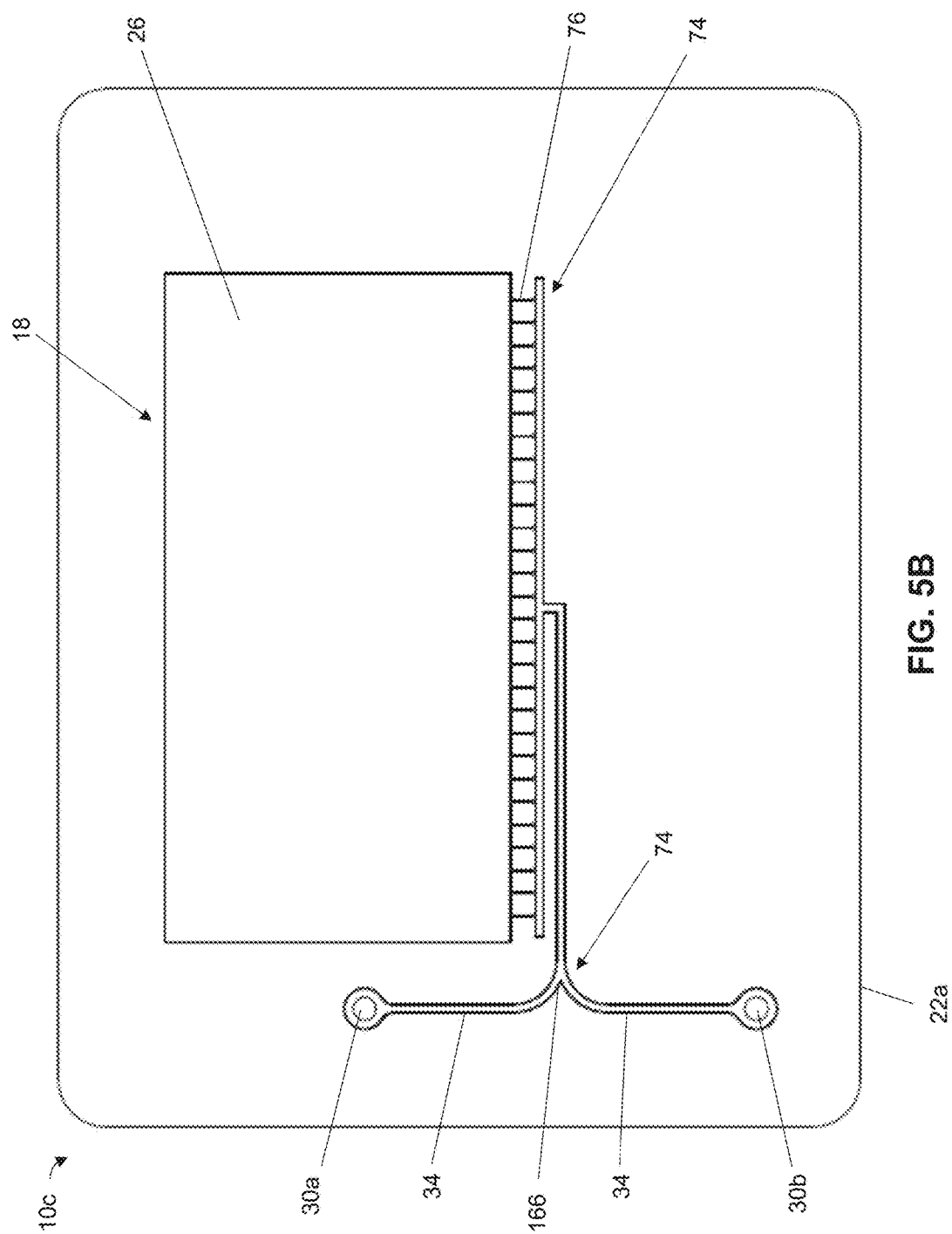

Referring to FIGS. 5A and 5B, shown is a microfluidic chip 10c that is substantially similar to chip 10a, the primary exception being that microfluidic network 18 of chip 10c comprises two or more ports (e.g., 30a and 30b) such as, for example, greater than or equal to or between any two of 2, 3, 4, 5, 6, 7, 8, or more ports. As shown, microfluidic network 18 comprises two ports 30a and 30b. At least a portion of each of ports 30a and 30b can be defined by a respective one of protrusions 70a and 70b that extend from top face 62a of planar portion 58.

Two or more channels 34 can place ports 30a and 30b in fluid communication with test volume 26 such that the ports are disposed upstream, and connected to one another independently of, the test volume. For example, microfluidic network 18 can be configured such that, for each of ports 30a and 30b, fluid can flow from the port to each other of the ports without flowing through test volume 26. As configured, microfluidic network 18 can prevent gas from being (e.g., inadvertently) drawn into chip 10c and test volume 26 via one of ports 30a and 30b when pressure is reduced at at least one other of the ports (e.g., during gas evacuation).

In at least one of droplet-generating region(s) 74, two or more of channels 34 can connect at a junction 166 (e.g., a T-junction) at which liquid that enters chip 10c via a respective one of ports 30a and 30b can meet before flowing to test volume 26. For example, for each of at least two of channels 34 connected at junction 166, fluids can flow from at least one of ports 30a and 30b, through the connecting channel, and to the junction without flowing through any other of the connecting channels or test volume 26. Liquid droplets can be generated at junction 166. For example, a first (e.g., non-aqueous) liquid can be introduced into port 30a and a second (e.g., aqueous) liquid can be introduced into port 30b. Microfluidic network 18 can be configured such that, at junction 166, the first liquid can flow faster than and thereby shear the second liquid to form droplets. To achieve different flow rates, the connecting channel(s) 34 through which the first fluid flows can, for example, have a smaller cross-sectional area than those through which the second fluid flows. At least one of droplet-generating region(s) 74 can have a junction 166 additionally or alternatively to a constriction section 76 and expansion region 98.

Referring to FIG. 6, shown is a microfluidic chip 10d that is substantially similar to chip 10a, the primary exception being that body 14 of chip 10d defines multiple microfluidic networks 18. Each of microfluidic networks 18 can be substantially the same as that of chip 10a, chip 10b, or chip 10c. Incorporating multiple microfluidic networks 18 into chip 10d can, for example, facilitate simultaneous analysis of multiple liquids and can increase throughput. At least one of the piece(s) (e.g., 22a and 22b) of body 14 can be formed using a lithographically-produced mold such that microfluidic networks 18 are defined with a suitable level of precision.

Referring to FIG. 7, shown is a system 170 that can be used to load a test volume 26 of one or more of the present microfluidic chips (e.g., 10a-10d). System 170 can comprise a vacuum chamber 174 configured to receive and contain the microfluidic chip(s). A vacuum source 178 and one or more control valves (e.g., 182a-182d) can be configured to adjust the pressure within vacuum chamber 174. For example, vacuum source 178 can be configured to remove gas from vacuum chamber 174 and thereby decrease the pressure therein (e.g., to below the ambient pressure) and thus at the port(s) (e.g., 30, 30a-30b) of each of the microfluidic chip(s). The decreased pressure can facilitate gas evacuation of the microfluidic chip(s). Each of the control valve(s) can be movable between closed and open positions in which the control valve prevents and permits, respectively, fluid transfer between vacuum chamber 174, vacuum source 178, and/or and external environment 186. For example, after a vacuum is generated in vacuum chamber 174, opening at least one of the control valve(s) can permit gas to enter the vacuum chamber (e.g., from external environment 186) to increase the pressure therein (e.g., to the ambient pressure) and thus at the port(s) of each of the microfluidic chip(s). The increased pressure can facilitate droplet generation and liquid loading of test volume 26.

System 170 can comprise a controller 190 configured to control vacuum source 178 and/or the control valve(s) to regulate pressure in vacuum chamber 174. Controller 190 can be configured to receive vacuum chamber pressure measurements from a pressure sensor 194. Based at least in part on those pressure measurements, controller 190 can be configured to activate vacuum source 178 and/or at least one of the control valve(s), e.g., to achieve a target pressure within vacuum chamber 174 (e.g., with a proportional-integral-derivative controller). For example, the control valve(s) of system 170 can comprise a slow valve 182a and a fast valve 182b, each—when in the open position—permitting fluid flow between vacuum chamber 174 and at least one of vacuum source 178 and external environment 186. System 170 can be configured such that the maximum rate at which gas can flow through slow valve 182a is lower than that at which gas can flow through fast valve 182b. As shown, for example, system 170 comprises a restriction 198 in fluid communication with slow valve 182a. Controller 190 can control the rate at which gas enters or exits vacuum chamber 174—and thus the rate of change of pressure in the vacuum chamber—at least by selecting and opening at least one of slow valve 182a (e.g., for a low flow rate) and fast valve 182b (e.g., for a high flow rate) and closing the non-selected valve(s), if any. As such, suitable control can be achieved without the need for a variable-powered vacuum source or proportional valves, although, in some embodiments, vacuum source 178 can provide different levels of vacuum power and/or at least one of control valves 182a-182d can comprise a proportional valve.

The control valve(s) of system 170 can comprise a vacuum valve 182c and a vent valve 182d. During gas evacuation, vacuum valve 182c can be opened and vent valve 182d can be closed such that vacuum source 178 can draw gas from vacuum chamber 174 and the vacuum chamber is isolated from external environment 186. During liquid introduction, vacuum valve 182c can be closed and vent valve 182d can be opened such that gas (e.g., air) can flow from external environment 186 into vacuum chamber 174. Slow and fast valves 182a and 182b can be in fluid communication with both vacuum valve 182c and vent valve 182d such that controller 190 can adjust the flow rate in or out of vacuum chamber 174 with the slow and fast valves during both stages.

Referring to FIGS. 8A-8D, shown is a schematic illustrating some of the present methods of loading a microfluidic chip (e.g., 10). The chip can comprise any of the chips described above (e.g., 10a-10d), and can have any of the above-described features (e.g., port(s), channel(s), test volume, constriction(s), expansion region(s), junction(s), and/ or the like). Some methods comprise disposing a liquid (e.g., 202) within a first one of the port(s) (e.g., 30 and/or 30a and 30b) of the microfluidic network (e.g., 18) of the chip (FIG. 8B). The first port can be the only port of the microfluidic network (e.g., as in chips 10a-10b and 10d,) or can be one of two or more ports (e.g., as in chip 10c) of the microfluidic network. The liquid can comprise an aqueous liquid (e.g., 206) (e.g., a liquid containing a sample for analysis, such as a pathogen or a medication) and a non-aqueous liquid (e.g., 210) (e.g., oil). The disposing can be performed by (e.g., sequentially) disposing the non-aqueous liquid and the aqueous liquid in the first port such that the aqueous liquid is disposed above the non-aqueous liquid.

Some methods comprise a step of reducing pressure at the first port such that gas (e.g., 214) flows from the test volume (e.g., 26), through at least one of the channel(s) (e.g., 34), and out of the first port (FIG. 8C). Gas that flows out of the first port can pass through the liquid. As described above, the relative dimensions of the first port and the channel(s) connected thereto can facilitate bubble formation as the gas passes through the liquid. Advantageously, the gas bubbles can agitate and thereby mix the aqueous liquid to facilitate loading and/or analysis thereof in the test volume.

Prior to the pressure reduction, the pressure at the first port (and, optionally, in the test volume) can be substantially ambient pressure; to evacuate gas from the test volume, the pressure at the first port can be reduced below ambient pressure. For example, reducing pressure can be performed such that the pressure at the first port is less than or equal to, or between any two of, 0.5, 0.4, 0.3, 0.2, 0.1, or 0 atm. Greater pressure reductions can increase the amount of gas evacuated from the test volume.

The pressure reductions can be achieved using any suitable system, such as, for example, system 170 of FIG. 7. For example, the chip can be disposed within a vacuum chamber (e.g., 174) that is at substantially atmospheric pressure. The pressure can be reduced in the vacuum chamber (e.g., at least by actuating a vacuum source (e.g., 178) and/or opening at least one of one or more control valves (e.g., 182a-182d) to permit gas withdrawal from the vacuum chamber) and thus at the first port (and, optionally, at any other port(s) of the chip). A fast valve (e.g., 182b) and a vacuum valve (e.g., 182c) can be opened such that the vacuum source can draw gas from the vacuum chamber at a comparatively high flow rate.

Some methods comprise a step of increasing pressure at the first port such that at least a portion of the liquid flows from the first port, through one or more of the droplet-generating region(s) (e.g., 74) defined by the microfluidic network, and into the test volume (FIG. 8D). When flowing through the droplet-generating region(s), the portion of the liquid (e.g., the aqueous liquid) can form into droplets (e.g., 218) as described above. For example, referring additionally to FIGS. 9A-9D, droplet formation can occur as the portion of the liquid passes through a constriction section (e.g., 76) defining a constriction (e.g., 78) followed by an expansion region (e.g., 98). A first droplet can form as liquid exits the constriction section via a constriction outlet (e.g., 86) into a constant portion (e.g., 118) of the expansion region (FIGS. 9A and 9B). The constant portion can compress the first droplet. A subsequently-formed droplet can urge the first droplet into an expanding portion (e.g., 122) in which the first droplet travels and expands along a ramp (e.g., 142). The process can repeat to form multiple droplets, with the ramp mitigating obstruction of the constriction outlet to maintain a consistent droplet size.

Additionally, or alternatively, droplet formation can occur at a junction (e.g., 166) where two or more of the channels connect. To illustrate, the microfluidic network can comprise two or more ports and disposing can be performed such that the aqueous liquid is placed in the first port and the non-aqueous liquid is placed in a second one of the ports. After gas evacuation, pressure can be increased at both the first and second ports such that each of the aqueous and non-aqueous liquids flows through respective one(s) of the channels connected to the junction. The aqueous and non-aqueous liquids can meet at the junction, where the non-aqueous liquid can shear the aqueous liquid to form aqueous droplets. The non-aqueous liquid can flow faster than the aqueous liquid at the junction to facilitate shearing; for example, of the channels connected to the junction, at least one of those through which the non-aqueous liquid flows can have a smaller cross-sectional area than those through which the aqueous liquid flows.

If the vacuum chamber is used (e.g., that of system 170), the pressure increase can be achieved by venting the vacuum chamber such that gas flows therein. Venting can be performed by controlling one or more of the control valve(s) to permit gas (e.g., air) to enter the vacuum chamber. For example, a vent valve (e.g., 182d) and at least one of the slow and fast valves can be opened such that gas from the external environment (e.g., 186) flows into the vacuum chamber. The rate at which gas flows into the vacuum chamber, and thus the rate at which liquid flows toward the test volume, can be controlled using the control valve(s). To illustrate, the fast valve can be opened first such that gas flows into the vacuum chamber at a relatively high rate. When the fast valve is open, the portion of the liquid can reach the droplet generating region(s) relatively quickly. The fast valve can thereafter be closed and the slow valve can be opened such that gas flows into the vacuum chamber at a relatively lower rate. Doing so can decrease the flow rate of the portion of the liquid, which can facilitate droplet formation.

Increasing the pressure at the first port can be performed such that, after the pressure increase, the pressure at the first port is substantially ambient pressure. As the liquid is introduced into the test volume, the pressure within the test volume can increase until it reaches substantially ambient pressure as well. By achieving pressure equalization between the test volume and the environment outside of the chip (e.g., to ambient pressure), the position of the droplets within the test volume can be maintained for analysis without the need for additional seals or other retention mechanisms. Conventionally-loaded chips may require additional mechanisms for pressure equalization—these mechanisms can require additional non-aqueous liquid (e.g., oil) to protect the droplets from air. The present chips and loading methods thereof, because they obviate the need for such mechanisms, can reduce the amount of non-aqueous liquid required to load the chip, thereby reducing costs.

Evacuating at least some of the test volume gas before introducing the liquid can provide other benefits as well. Gas in the test volume can cause evaporation of the aqueous liquid droplets disposed therein due to phase displacement; decreasing the amount of test volume gas can mitigate this risk. Evacuating gas from the test volume can reduce the pressure in the test volume such that liquid loading is achieved with a negative pressure gradient, e.g., in which the pressure in the test volume is below that outside of the chip. The negative pressure gradient can reinforce seals (e.g., between different pieces of the body) to prevent chip delamination and can contain unintentional leaks by drawing gas into a leak if there is a failure. Leak containment can promote safety when, for example, the aqueous liquid contains pathogens.

The claims are not intended to include, and should not be interpreted to include, means-plus- or step-plus-function limitations, unless such a limitation is explicitly recited in a given claim using the phrase(s) "means for" or "step for," respectively.

The invention claimed is:

1. A microfluidic chip comprising:
a body; and
one or more microfluidic networks defined by the body, at least one of the network(s) including:
a single port;
a test volume; and
one or more channels in fluid communication between the port and the test volume, the network defining one or more droplet-generating regions in which at least one of the channel(s) defines a constriction.

2. The chip of claim 1, wherein, for each of the port(s):
the port has a minimum cross-sectional area, taken perpendicularly to the centerline of the port; and
for each of the channel(s) connected to the port, the portion of the channel that connects to the port has a minimum cross-sectional area, taken perpendicularly to the centerline of the portion of the channel, that is less than or equal to 90% of the minimum cross-sectional area of the port.

3. The chip of claim 1, wherein each of the channel(s) has a maximum transverse dimension, taken perpendicularly to the centerline of the channel, that is less than 2 millimeters (mm).

4. The chip of claim 1, wherein the body comprises:
a planar portion having top and bottom faces connected by an edge, the planar portion defining the test volume and the channel(s); and
one or more protrusions extending from the top face, each of the protrusion(s) defining at least a portion of at least one of the port(s).

5. The chip of claim 1, wherein for at least one of the network(s):
the network includes an expansion region; and
in at least one of the droplet-generating region(s), at least one of the channel(s) comprises a constriction section that defines the constriction and is connected to the expansion region such that liquid is permitted to flow from the port, pass through the constriction section, and exit the constriction section into the expansion region;
wherein a minimum cross-sectional area of the expansion region is greater than or equal to 110% of a minimum cross-sectional area of the constriction section, taken perpendicularly to the centerline of the constriction section.

6. The chip of claim 5, wherein the expansion region has:
a minimum height that is greater than or equal to 150% of a maximum height of each of the constriction section(s), taken perpendicularly to the centerline of the constriction section; and
a constant portion and an expanding portion such that liquid is permitted to exit at least one of the constriction section(s) into the constant portion and flow to the expanding portion, wherein:
the constant portion has a height that is substantially the same between the constriction section and the expanding portion and is substantially equal to the minimum height of the expansion region; and
the expanding portion has a height that increases moving away from the constant portion.

7. A method of loading a microfluidic chip, the method comprising:
disposing a liquid that comprises an aqueous liquid and a non-aqueous liquid within a first one of one or more ports of a microfluidic network of a microfluidic chip, the network including:
a test volume; and
one or more channels in fluid communication between the port(s) and the test volume, the network defining one or more droplet-generating regions in which:
at least one of the channel(s) defines a constriction; and/or
two or more of the channel(s) connect at a junction, wherein, for each of at least two of the connecting channels, fluid is permitted to flow from at least one of the port(s), through the connecting channel, and to the junction without flowing through any other of the connecting channels or the test volume; and
introducing at least a portion of the liquid into the test volume at least by:
(1) reducing pressure at the first port such that gas flows from the test volume, through at least one of the channel(s), and out of the first port; and
(2) increasing pressure at the first port such that the portion of the liquid flows from the first port, through at least one of the droplet-generating region(s), and into the test volume.

8. The method of claim 7, wherein the port(s) consist of the first port.

9. The method of claim 7, wherein:
the port(s) comprise two or more ports; and
the network is configured such that, for each of the ports, fluid is permitted to flow from the port to each other of the ports without flowing through the test volume.

10. The method of claim 7, wherein:
the first port has a minimum cross-sectional area, taken perpendicularly to the centerline of the first port; and
for each of the channel(s) connected to the first port, the portion of the channel that connects to the first port has a minimum cross-sectional area, taken perpendicularly to the centerline of the portion of the channel, that is less than or equal to 90% of the minimum cross-sectional area of the first port.

11. The method of claim 7, wherein each of the channel(s) has a maximum transverse dimension, taken perpendicularly to the centerline of the channel, that is less than 2 mm.

12. The method of claim 7, wherein:
the network includes an expansion region; and
in at least one of the droplet-generating region(s), at least one of the channel(s) comprises a constriction section that defines the constriction and is connected to the expansion region such that when pressure at the first port is increased, the portion of the liquid flows from the first port, passes through the constriction section, and exits the constriction section into the expansion region;
wherein a minimum cross-sectional area of the expansion region is greater than or equal to 110% of a minimum cross-sectional area of the constriction section, taken perpendicularly to the centerline of the constriction section.

13. The method of claim 12, wherein the expansion region has:
- a minimum height that is greater than or equal to 150% of a maximum height of each of the constriction section(s), taken perpendicularly to the centerline of the constriction section; and
- a constant portion and an expanding portion such that when the portion of the liquid exits the constriction section, the portion of the liquid enters into the constant portion and flows to the expanding portion, wherein:
  - the constant portion has a height that is substantially the same between the constriction section and the expanding portion and is substantially equal to the minimum height of the expansion region; and
  - the expanding portion has a height that increases moving away from the constant portion.

14. The method of claim 7, wherein reducing pressure at the first port is performed at least by reducing pressure within a vacuum chamber within which the chip is disposed.

15. The method of claim 14, wherein increasing pressure at the first port is performed at least by venting the vacuum chamber.

16. The method of claim 7, wherein, during reducing pressure at the first port, gas that flows out of the first port passes through the liquid.

17. The method of claim 7, wherein:
- prior to reducing pressure at the first port, pressure at the first port is substantially ambient pressure; and
- after increasing pressure at the first port, pressure at the first port is substantially ambient pressure.

18. The method of claim 17, wherein, after introducing at least a portion of the liquid into the test volume, pressure within the test volume is substantially ambient pressure.

* * * * *